(12) United States Patent
Auyoung et al.

(10) Patent No.: US 8,317,831 B2
(45) Date of Patent: Nov. 27, 2012

(54) INTERSPINOUS PROCESS SPACER DIAGNOSTIC BALLOON CATHETER AND METHODS OF USE

(75) Inventors: Bryan J. Auyoung, Santa Clara, CA (US); Reynaldo A. Osorio, Daly City, CA (US)

(73) Assignee: Kyphon SARL, Neuchatel (CH)

( * ) Notice: Subject to any disclaimer, the term of this patent is extended or adjusted under 35 U.S.C. 154(b) by 367 days.

(21) Appl. No.: 12/686,617

(22) Filed: Jan. 13, 2010

(65) Prior Publication Data
US 2011/0172596 A1 Jul. 14, 2011

(51) Int. Cl.
*A61M 29/00* (2006.01)
(52) U.S. Cl. ..................... 606/249; 604/96.01
(58) Field of Classification Search .......... 600/206–208; 606/90, 102, 191–192, 247–249, 915; 623/17.11–17.16
See application file for complete search history.

(56) References Cited

U.S. PATENT DOCUMENTS

| | | | |
|---|---|---|---|
| 624,969 A | 5/1899 | Peterson |
| 1,153,797 A | 9/1915 | Kegreisz |
| 1,516,347 A | 11/1924 | Pataky |
| 1,870,942 A | 8/1932 | Beatty |
| 2,077,804 A | 4/1937 | Morrison |
| 2,299,308 A | 10/1942 | Creighton |
| 2,485,531 A | 10/1949 | Dzus et al. |
| 2,607,370 A | 8/1952 | Anderson |
| 2,677,369 A | 5/1954 | Knowles |
| 2,685,877 A | 8/1954 | Dobelle |
| 3,065,659 A | 11/1962 | Eriksson et al. |
| 3,108,595 A | 10/1963 | Overment |
| 3,397,699 A | 8/1968 | Kohl |
| 3,426,364 A | 2/1969 | Lumb |
| 3,648,691 A | 3/1972 | Lumb et al. |
| 3,779,239 A | 12/1973 | Fischer et al. |
| 3,860,969 A | 1/1975 | Arion |
| 3,867,728 A | 2/1975 | Stubstad et al. |
| 4,011,602 A | 3/1977 | Rybicki et al. |
| 4,237,875 A | 12/1980 | Termanini |
| 4,257,409 A | 3/1981 | Bacal et al. |

(Continued)

FOREIGN PATENT DOCUMENTS
DE 2821678 A1 11/1979
(Continued)

OTHER PUBLICATIONS

Anasetti et al., "Spine Stability After Implantation of an Interspinous Device: An in Vitro and Finite Element Biomechanical Study," J. Neurosurg. Spine, Nov. 2010, vol. 13, pp. 568-575.

(Continued)

*Primary Examiner* — Kevin T Truong
*Assistant Examiner* — Christopher Beccia
(74) *Attorney, Agent, or Firm* — Sorell, Lenna & Schmidt, LLP

(57) ABSTRACT

An interspinous process spacer diagnostic balloon catheter and method. The balloon catheter has a main expandable member, a distal expandable member and a proximal expandable member that all can be expanded from a collapsed configuration to an expanded configuration and then collapsed again to a collapsed configuration. The device can be used to determine whether a particular patient is a candidate for implantation of an interspinous process spacer to treat the symptoms of lumbar spinal stenosis and the size of such a spacer if indicated.

20 Claims, 9 Drawing Sheets

U.S. PATENT DOCUMENTS

| | | | |
|---|---|---|---|
| 4,274,324 A | 6/1981 | Giannuzzi | |
| 4,289,123 A | 9/1981 | Dunn | |
| 4,327,736 A | 5/1982 | Inoue | |
| 4,401,112 A | 8/1983 | Rezaian | |
| 4,499,636 A | 2/1985 | Tanaka | |
| 4,519,100 A | 5/1985 | Wills et al. | |
| 4,553,273 A | 11/1985 | Wu | |
| 4,554,914 A | 11/1985 | Kapp et al. | |
| 4,573,454 A | 3/1986 | Hoffman | |
| 4,573,966 A | 3/1986 | Weikl et al. | |
| 4,592,341 A | 6/1986 | Omagari et al. | |
| 4,599,086 A | 7/1986 | Doty | |
| 4,604,995 A | 8/1986 | Stephens et al. | |
| 4,610,662 A | 9/1986 | Weikl et al. | |
| 4,611,582 A | 9/1986 | Duff | |
| 4,632,101 A | 12/1986 | Freedland | |
| 4,636,217 A | 1/1987 | Ogilvie et al. | |
| 4,646,998 A | 3/1987 | Pate | |
| 4,657,550 A | 4/1987 | Daher | |
| 4,662,808 A | 5/1987 | Camilleri | |
| 4,686,970 A | 8/1987 | Dove et al. | |
| 4,704,057 A | 11/1987 | McSherry | |
| 4,721,103 A | 1/1988 | Freedland | |
| 4,759,769 A | 7/1988 | Hedman et al. | |
| 4,787,378 A | 11/1988 | Sodhi | |
| 4,822,226 A | 4/1989 | Kennedy | |
| 4,827,918 A | 5/1989 | Olerud | |
| 4,834,600 A | 5/1989 | Lemke | |
| 4,863,476 A | 9/1989 | Shepperd | |
| 4,886,405 A | 12/1989 | Blomberg | |
| 4,892,545 A | 1/1990 | Day et al. | |
| 4,913,144 A | 4/1990 | Del Medico | |
| 4,931,055 A | 6/1990 | Bumpus et al. | |
| 4,932,975 A | 6/1990 | Main et al. | |
| 4,969,887 A | 11/1990 | Sodhi | |
| 4,969,888 A | 11/1990 | Scholten et al. | |
| 5,000,166 A | 3/1991 | Karpf | |
| 5,011,484 A | 4/1991 | Breard | |
| 5,019,042 A | 5/1991 | Sahota | |
| 5,035,712 A | 7/1991 | Hoffman | |
| 5,047,055 A | 9/1991 | Bao et al. | |
| 5,059,193 A | 10/1991 | Kuslich | |
| 5,092,866 A | 3/1992 | Breard et al. | |
| 5,098,433 A | 3/1992 | Freedland | |
| 5,112,306 A | 5/1992 | Burton et al. | |
| 5,171,278 A | 12/1992 | Pisharodi | |
| 5,171,280 A | 12/1992 | Baumgartner | |
| 5,201,734 A | 4/1993 | Cozad et al. | |
| 5,267,999 A | 12/1993 | Olerud | |
| 5,290,312 A | 3/1994 | Kojimoto et al. | |
| 5,306,275 A | 4/1994 | Bryan | |
| 5,306,310 A | 4/1994 | Siebels | |
| 5,312,405 A | 5/1994 | Korotko et al. | |
| 5,316,422 A | 5/1994 | Coffman | |
| 5,330,429 A | 7/1994 | Noguchi et al. | |
| 5,342,305 A | 8/1994 | Shonk | |
| 5,356,423 A | 10/1994 | Tihon et al. | |
| 5,358,487 A | 10/1994 | Miller | |
| 5,360,430 A | 11/1994 | Lin | |
| 5,366,455 A | 11/1994 | Dove | |
| 5,370,697 A | 12/1994 | Baumgartner | |
| 5,390,683 A | 2/1995 | Pisharodi | |
| 5,395,370 A | 3/1995 | Muller et al. | |
| 5,401,269 A | 3/1995 | Buttner-Janz et al. | |
| 5,403,316 A | 4/1995 | Ashman | |
| 5,415,661 A | 5/1995 | Holmes | |
| 5,437,672 A | 8/1995 | Alleyne | |
| 5,437,674 A | 8/1995 | Worcel et al. | |
| 5,439,463 A | 8/1995 | Lin | |
| 5,454,812 A | 10/1995 | Lin | |
| 5,456,689 A | 10/1995 | Kresch et al. | |
| 5,458,641 A | 10/1995 | Ramirez Jimenez | |
| 5,460,610 A | 10/1995 | Don Michael | |
| 5,480,442 A | 1/1996 | Bertagnoli | |
| 5,496,318 A | 3/1996 | Howland et al. | |
| 5,518,498 A | 5/1996 | Lindenberg et al. | |
| 5,540,689 A | 7/1996 | Sanders et al. | |
| 5,549,679 A | 8/1996 | Kuslich | |
| 5,554,191 A | 9/1996 | Lahille et al. | |
| 5,562,662 A | 10/1996 | Brumfield et al. | |
| 5,562,735 A | 10/1996 | Margulies | |
| 5,562,736 A | 10/1996 | Ray et al. | |
| 5,571,192 A | 11/1996 | Schonhoffer | |
| 5,609,634 A | 3/1997 | Voydeville | |
| 5,609,635 A | 3/1997 | Michelson | |
| 5,628,756 A | 5/1997 | Barker, Jr. et al. | |
| 5,630,816 A | 5/1997 | Kambin | |
| 5,645,597 A | 7/1997 | Krapiva | |
| 5,645,599 A | 7/1997 | Samani | |
| 5,653,762 A | 8/1997 | Pisharodi | |
| 5,653,763 A | 8/1997 | Errico et al. | |
| 5,658,335 A | 8/1997 | Allen | |
| 5,665,122 A | 9/1997 | Kambin | |
| 5,674,295 A * | 10/1997 | Ray et al. | 623/17.12 |
| 5,676,702 A | 10/1997 | Ratron | |
| 5,685,826 A | 11/1997 | Bonutti | |
| 5,690,649 A | 11/1997 | Li | |
| 5,693,100 A | 12/1997 | Pisharodi | |
| 5,702,391 A | 12/1997 | Lin | |
| 5,702,395 A | 12/1997 | Hopf | |
| 5,702,452 A | 12/1997 | Argenson et al. | |
| 5,702,454 A | 12/1997 | Baumgartner | |
| 5,702,455 A | 12/1997 | Saggar | |
| 5,707,390 A | 1/1998 | Bonutti | |
| 5,716,416 A | 2/1998 | Lin | |
| 5,723,013 A | 3/1998 | Jeanson et al. | |
| 5,725,341 A | 3/1998 | Hofmeister | |
| 5,746,762 A | 5/1998 | Bass | |
| 5,749,916 A | 5/1998 | Richelsoph | |
| 5,755,797 A | 5/1998 | Baumgartner | |
| 5,800,547 A | 9/1998 | Schafer et al. | |
| 5,800,549 A | 9/1998 | Bao et al. | |
| 5,810,815 A | 9/1998 | Morales | |
| 5,836,948 A | 11/1998 | Zucherman et al. | |
| 5,849,004 A | 12/1998 | Bramlet | |
| 5,860,977 A | 1/1999 | Zucherman et al. | |
| 5,888,196 A | 3/1999 | Bonutti | |
| 5,941,881 A | 8/1999 | Barnes | |
| 5,964,730 A | 10/1999 | Williams et al. | |
| 5,976,186 A | 11/1999 | Bao et al. | |
| 5,980,523 A | 11/1999 | Jackson | |
| 6,022,376 A | 2/2000 | Assell et al. | |
| 6,048,342 A | 4/2000 | Zucherman et al. | |
| 6,066,154 A * | 5/2000 | Reiley et al. | 606/192 |
| 6,068,630 A | 5/2000 | Zucherman et al. | |
| 6,074,390 A | 6/2000 | Zucherman et al. | |
| 6,102,922 A | 8/2000 | Jakobsson et al. | |
| 6,126,689 A | 10/2000 | Brett | |
| 6,126,691 A | 10/2000 | Kasra et al. | |
| 6,127,597 A | 10/2000 | Beyar et al. | |
| 6,132,464 A | 10/2000 | Martin | |
| 6,190,413 B1 | 2/2001 | Sutcliffe | |
| 6,190,414 B1 | 2/2001 | Young | |
| 6,214,037 B1 | 4/2001 | Mitchell et al. | |
| 6,214,050 B1 | 4/2001 | Huene | |
| 6,245,107 B1 | 6/2001 | Ferree | |
| 6,293,949 B1 | 9/2001 | Justis et al. | |
| 6,336,930 B1 | 1/2002 | Stalcup et al. | |
| 6,348,053 B1 | 2/2002 | Cachia | |
| 6,352,537 B1 | 3/2002 | Strnad | |
| 6,364,883 B1 | 4/2002 | Santilli | |
| 6,371,987 B1 | 4/2002 | Weiland et al. | |
| 6,375,682 B1 | 4/2002 | Fleischmann et al. | |
| 6,402,750 B1 | 6/2002 | Atkinson et al. | |
| 6,402,751 B1 | 6/2002 | Hoeck et al. | |
| 6,419,703 B1 | 7/2002 | Fallin et al. | |
| 6,419,704 B1 | 7/2002 | Ferree | |
| 6,432,130 B1 | 8/2002 | Hanson | |
| 6,436,140 B1 | 8/2002 | Liu et al. | |
| 6,440,169 B1 | 8/2002 | Elberg et al. | |
| 6,447,513 B1 | 9/2002 | Griggs | |
| 6,447,546 B1 | 9/2002 | Bramlet et al. | |
| 6,451,019 B1 | 9/2002 | Zucherman et al. | |
| 6,485,456 B1 * | 11/2002 | Kletschka | 604/96.01 |
| 6,500,178 B2 | 12/2002 | Zucherman et al. | |
| 6,511,508 B1 | 1/2003 | Shahinpoor et al. | |
| 6,514,256 B2 | 2/2003 | Zucherman et al. | |

| | | |
|---|---|---|
| 6,520,991 B2 | 2/2003 | Huene |
| 6,527,803 B1 | 3/2003 | Crozet et al. |
| 6,554,833 B2 | 4/2003 | Levy |
| 6,572,653 B1 | 6/2003 | Simonson |
| 6,582,433 B2 | 6/2003 | Yun |
| 6,582,467 B1 | 6/2003 | Teitelbaum et al. |
| 6,592,585 B2 | 7/2003 | Lee et al. |
| 6,610,069 B2 | 8/2003 | Euteneuer et al. |
| 6,626,944 B1 | 9/2003 | Taylor |
| 6,645,207 B2 | 11/2003 | Dixon et al. |
| 6,669,729 B2 | 12/2003 | Chin |
| 6,685,742 B1 | 2/2004 | Jackson |
| 6,695,842 B2 | 2/2004 | Zucherman et al. |
| 6,699,246 B2 | 3/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,531 B1 | 5/2004 | Trieu |
| 6,733,533 B1 | 5/2004 | Lozier |
| 6,733,534 B2 * | 5/2004 | Sherman ................ 623/17.16 |
| 6,736,818 B2 | 5/2004 | Perren et al. |
| 6,743,257 B2 | 6/2004 | Castro |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |
| 6,835,205 B2 | 12/2004 | Atkinson et al. |
| 6,902,580 B2 | 6/2005 | Fallin et al. |
| 6,905,512 B2 | 6/2005 | Paes et al. |
| 6,946,000 B2 | 9/2005 | Senegas et al. |
| 6,958,077 B2 * | 10/2005 | Suddaby ................ 623/17.11 |
| 6,969,404 B2 | 11/2005 | Ferree |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,070,598 B2 | 7/2006 | Lim et al. |
| 7,081,120 B2 | 7/2006 | Li et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,097,654 B1 | 8/2006 | Freedland |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 * | 10/2008 | Mathieu et al. ............ 623/17.11 |
| 7,442,210 B2 | 10/2008 | Segal et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 7,641,673 B2 | 1/2010 | Le Couedic et al. |
| 7,658,752 B2 | 2/2010 | Labrom et al. |
| 7,666,205 B2 * | 2/2010 | Weikel et al. ................ 606/192 |
| 7,749,252 B2 | 7/2010 | Zucherman et al. |
| 7,771,456 B2 | 8/2010 | Hartmann et al. |
| 7,824,431 B2 | 11/2010 | McCormack |
| 7,862,615 B2 | 1/2011 | Carli et al. |
| 7,901,430 B2 | 3/2011 | Matsuura et al. |
| 7,927,354 B2 | 4/2011 | Edidin et al. |
| 7,942,847 B2 | 5/2011 | Stupecky et al. |
| 8,147,526 B2 * | 4/2012 | Auyoung ................ 606/279 |
| 2001/0016743 A1 | 8/2001 | Zucherman et al. |
| 2001/0049527 A1 | 12/2001 | Cragg |
| 2002/0082600 A1 | 6/2002 | Shaolian et al. |
| 2002/0143331 A1 | 10/2002 | Zucherman et al. |
| 2002/0177866 A1 | 11/2002 | Weikel et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2003/0176925 A1 | 9/2003 | Paponneau |
| 2004/0010312 A1 | 1/2004 | Enayati |
| 2004/0010316 A1 | 1/2004 | William et al. |
| 2004/0064094 A1 | 4/2004 | Freyman |
| 2004/0083002 A1 | 4/2004 | Belef et al. |
| 2004/0087947 A1 | 5/2004 | Lim et al. |
| 2004/0097931 A1 | 5/2004 | Mitchell |
| 2004/0098015 A1 * | 5/2004 | Weikel et al. ................ 606/192 |
| 2004/0106995 A1 | 6/2004 | LeCouedic et al. |
| 2004/0117017 A1 | 6/2004 | Pasquet et al. |
| 2004/0133204 A1 | 7/2004 | Davies |
| 2004/0133280 A1 | 7/2004 | Trieu |
| 2004/0158248 A1 | 8/2004 | Ginn |
| 2004/0167625 A1 | 8/2004 | Beyar et al. |
| 2004/0172029 A1 | 9/2004 | Lerch |
| 2004/0186577 A1 | 9/2004 | Ferree |
| 2004/0199255 A1 | 10/2004 | Mathieu et al. |
| 2004/0260239 A1 | 12/2004 | Kusleika |
| 2004/0260397 A1 | 12/2004 | Lambrecht et al. |
| 2005/0004592 A1 | 1/2005 | Criscuolo |
| 2005/0010293 A1 | 1/2005 | Zucherman et al. |
| 2005/0015140 A1 | 1/2005 | deBeer |
| 2005/0033434 A1 | 2/2005 | Berry |
| 2005/0049590 A1 | 3/2005 | Alleyne et al. |
| 2005/0049708 A1 | 3/2005 | Atkinson et al. |
| 2005/0056292 A1 | 3/2005 | Cooper |
| 2005/0085814 A1 | 4/2005 | Sherman et al. |
| 2005/0143827 A1 | 6/2005 | Globerman et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0267579 A1 | 12/2005 | Reiley et al. |
| 2005/0273166 A1 | 12/2005 | Sweeney |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0047282 A1 | 3/2006 | Gordon |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 * | 6/2006 | Kim ................ 606/90 |
| 2006/0129239 A1 | 6/2006 | Kwak |
| 2006/0136060 A1 | 6/2006 | Taylor |
| 2006/0142858 A1 | 6/2006 | Colleran et al. |
| 2006/0149136 A1 | 7/2006 | Seto et al. |
| 2006/0149242 A1 | 7/2006 | Kraus et al. |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241643 A1 | 10/2006 | Lim et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |

| | | | | | | |
|---|---|---|---|---|---|---|
| 2006/0265074 A1 | 11/2006 | Krishna et al. | | 2008/0281361 A1 | 11/2008 | Vittur et al. |
| 2006/0271044 A1 | 11/2006 | Petrini et al. | | 2009/0062915 A1 | 3/2009 | Kohm et al. |
| 2006/0271049 A1 | 11/2006 | Zucherman et al. | | 2009/0099610 A1 | 4/2009 | Johnson et al. |
| 2006/0271061 A1 | 11/2006 | Beyer et al. | | 2009/0105766 A1 | 4/2009 | Thompson et al. |
| 2006/0282075 A1 | 12/2006 | Labrom et al. | | 2009/0105773 A1 | 4/2009 | Lange et al. |
| 2006/0282079 A1 | 12/2006 | Labrom et al. | | 2009/0234389 A1 | 9/2009 | Chuang et al. |
| 2006/0293662 A1 | 12/2006 | Boyer, II et al. | | 2009/0240283 A1 | 9/2009 | Carls et al. |
| 2006/0293663 A1 | 12/2006 | Walkenhorst et al. | | 2009/0264927 A1 | 10/2009 | Ginsberg et al. |
| 2007/0005064 A1 | 1/2007 | Anderson et al. | | 2009/0270802 A1* | 10/2009 | Nishide et al. ........... 604/103.05 |
| 2007/0010813 A1 | 1/2007 | Zucherman et al. | | 2009/0270918 A1 | 10/2009 | Attia et al. |
| 2007/0032790 A1 | 2/2007 | Aschmann et al. | | 2009/0292316 A1 | 11/2009 | Hess |
| 2007/0043362 A1 | 2/2007 | Malandain et al. | | 2009/0326538 A1 | 12/2009 | Sennett et al. |
| 2007/0043363 A1 | 2/2007 | Malandain et al. | | 2010/0036419 A1 | 2/2010 | Patel et al. |
| 2007/0049935 A1 | 3/2007 | Edidin et al. | | 2010/0121379 A1 | 5/2010 | Edmond |
| 2007/0073289 A1 | 3/2007 | Kwak et al. | | 2010/0191241 A1 | 7/2010 | McCormack et al. |
| 2007/0100340 A1 | 5/2007 | Lange et al. | | 2010/0204732 A1 | 8/2010 | Aschmann et al. |
| 2007/0112330 A1 | 5/2007 | Palasis | | 2010/0211101 A1 | 8/2010 | Blackwell et al. |
| 2007/0123861 A1 | 5/2007 | Dewey et al. | | 2010/0241167 A1 | 9/2010 | Taber et al. |
| 2007/0142915 A1 | 6/2007 | Altarac et al. | | 2010/0318190 A1 | 12/2010 | Collins et al. |
| 2007/0151116 A1 | 7/2007 | Malandain | | 2011/0054531 A1 | 3/2011 | Lamborne et al. |
| 2007/0162000 A1 | 7/2007 | Perkins | | 2011/0144692 A1 | 6/2011 | Saladin et al. |
| 2007/0162136 A1* | 7/2007 | O'Neil et al. ............... 623/17.12 | | 2011/0166600 A1 | 7/2011 | Lamborne et al. |
| 2007/0167945 A1 | 7/2007 | Lange et al. | | | | |
| 2007/0173822 A1 | 7/2007 | Bruneau et al. | | FOREIGN PATENT DOCUMENTS | | |
| 2007/0173823 A1 | 7/2007 | Dewey et al. | | DE | 3922044 A1 | 2/1991 |
| 2007/0173832 A1 | 7/2007 | Tebbe et al. | | DE | 4012622 C1 | 7/1991 |
| 2007/0191833 A1 | 8/2007 | Bruneau et al. | | DE | 202006018978 U1 | 2/2007 |
| 2007/0191834 A1 | 8/2007 | Bruneau et al. | | EP | 0322334 B1 | 2/1992 |
| 2007/0191837 A1 | 8/2007 | Trieu | | EP | 0767636 B1 | 1/1999 |
| 2007/0191838 A1 | 8/2007 | Bruneau et al. | | EP | 1004276 A1 | 5/2000 |
| 2007/0198091 A1 | 8/2007 | Boyer et al. | | EP | 1011464 B1 | 6/2000 |
| 2007/0225807 A1 | 9/2007 | Phan et al. | | EP | 1138268 A1 | 10/2001 |
| 2007/0225810 A1 | 9/2007 | Colleran et al. | | EP | 1148850 B1 | 10/2001 |
| 2007/0233068 A1 | 10/2007 | Bruneau et al. | | EP | 1148851 B1 | 10/2001 |
| 2007/0233074 A1 | 10/2007 | Anderson et al. | | EP | 1302169 A1 | 4/2003 |
| 2007/0233076 A1 | 10/2007 | Trieu | | EP | 1330987 A1 | 7/2003 |
| 2007/0233081 A1 | 10/2007 | Pasquet et al. | | EP | 1552797 A2 | 7/2005 |
| 2007/0233084 A1 | 10/2007 | Betz et al. | | EP | 1854433 A1 | 11/2007 |
| 2007/0233089 A1 | 10/2007 | DiPoto et al. | | EP | 1905392 A1 | 4/2008 |
| 2007/0250060 A1 | 10/2007 | Anderson et al. | | EP | 1982664 A1 | 10/2008 |
| 2007/0270823 A1 | 11/2007 | Trieu et al. | | FR | 2623085 A1 | 5/1989 |
| 2007/0270824 A1 | 11/2007 | Lim et al. | | FR | 2625097 A1 | 6/1989 |
| 2007/0270825 A1 | 11/2007 | Carls et al. | | FR | 2681525 A1 | 3/1993 |
| 2007/0270826 A1 | 11/2007 | Trieu et al. | | FR | 2700941 A1 | 8/1994 |
| 2007/0270827 A1 | 11/2007 | Lim et al. | | FR | 2703239 A1 | 10/1994 |
| 2007/0270828 A1 | 11/2007 | Bruneau et al. | | FR | 2707864 A1 | 1/1995 |
| 2007/0270829 A1 | 11/2007 | Carls et al. | | FR | 2717675 A1 | 9/1995 |
| 2007/0270834 A1* | 11/2007 | Bruneau et al. ................. 606/61 | | FR | 2722087 A1 | 1/1996 |
| 2007/0270874 A1 | 11/2007 | Anderson | | FR | 2722088 A1 | 1/1996 |
| 2007/0272259 A1 | 11/2007 | Allard et al. | | FR | 2724554 A1 | 3/1996 |
| 2007/0276368 A1 | 11/2007 | Trieu et al. | | FR | 2725892 A1 | 4/1996 |
| 2007/0276369 A1 | 11/2007 | Allard et al. | | FR | 2730156 A1 | 8/1996 |
| 2007/0276493 A1 | 11/2007 | Malandain et al. | | FR | 2731643 A1 | 9/1996 |
| 2007/0276496 A1 | 11/2007 | Lange et al. | | FR | 2775183 A1 | 8/1999 |
| 2007/0276497 A1 | 11/2007 | Anderson | | FR | 2799948 A1 | 4/2001 |
| 2007/0282443 A1 | 12/2007 | Globerman et al. | | FR | 2816197 A1 | 5/2002 |
| 2008/0021457 A1 | 1/2008 | Anderson et al. | | JP | 02-224660 | 9/1990 |
| 2008/0021460 A1 | 1/2008 | Bruneau et al. | | JP | 09-075381 | 3/1997 |
| 2008/0058934 A1 | 3/2008 | Malandain et al. | | JP | 2003079649 | 3/2003 |
| 2008/0097446 A1 | 4/2008 | Reiley et al. | | SU | 988281 | 1/1983 |
| 2008/0114357 A1 | 5/2008 | Allard et al. | | SU | 1484348 A1 | 6/1989 |
| 2008/0114358 A1 | 5/2008 | Anderson et al. | | WO | WO 94/26192 | 11/1994 |
| 2008/0114456 A1 | 5/2008 | Dewey et al. | | WO | WO 94/26195 | 11/1994 |
| 2008/0147190 A1 | 6/2008 | Dewey et al. | | WO | WO 97/18769 | 5/1997 |
| 2008/0161818 A1 | 7/2008 | Kloss et al. | | WO | WO 98/20939 | 5/1998 |
| 2008/0167685 A1 | 7/2008 | Allard et al. | | WO | WO 99/26562 | 6/1999 |
| 2008/0177306 A1 | 7/2008 | Lamborne et al. | | WO | WO 99/59669 | 11/1999 |
| 2008/0183209 A1 | 7/2008 | Robinson et al. | | WO | WO 00/44319 | 8/2000 |
| 2008/0183211 A1 | 7/2008 | Lamborne et al. | | WO | WO 01/54598 A1 | 8/2001 |
| 2008/0183218 A1 | 7/2008 | Mueller et al. | | WO | WO 03/057055 A1 | 7/2003 |
| 2008/0195152 A1 | 8/2008 | Altarac et al. | | WO | WO 2004/047689 A1 | 6/2004 |
| 2008/0208341 A1 | 8/2008 | McCormack et al. | | WO | WO 2004/047691 A1 | 6/2004 |
| 2008/0215094 A1 | 9/2008 | Taylor | | WO | WO 2004/084743 A1 | 10/2004 |
| 2008/0221685 A9 | 9/2008 | Altarac et al. | | WO | WO 2004/084768 A2 | 10/2004 |
| 2008/0234824 A1 | 9/2008 | Youssef et al. | | WO | WO 2004/110300 A2 | 12/2004 |
| 2008/0243250 A1 | 10/2008 | Seifert et al. | | WO | WO 2005/002474 A1 | 1/2005 |
| 2008/0262617 A1 | 10/2008 | Froehlich et al. | | WO | WO 2005/009300 A1 | 2/2005 |
| 2008/0281359 A1 | 11/2008 | Abdou | | WO | WO 2005/011507 A1 | 2/2005 |
| 2008/0281360 A1 | 11/2008 | Vittur et al. | | WO | WO 2005/044118 A1 | 5/2005 |

| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |
| WO | WO 2007052975 A1 | 5/2007 |
| WO | WO 2009/083276 A1 | 7/2009 |
| WO | WO 2009/083583 A1 | 7/2009 |
| WO | WO 2009/098536 A1 | 8/2009 |
| WO | WO 2009/149079 A1 | 12/2009 |
| WO | WO 2012/035275 A1 | 3/2012 |

OTHER PUBLICATIONS

Bellini et al., "Biomechanics of the Lumbar Spine After Dynamic Stabilization," J. Spinal Discord Tech., 2006, vol. 00, No. 00, pp. 1-7.
Bini et al., "Minimally Invasive Treatment of Moderate Lumbar Spinal Stenosis with the Superion® Interspinous Spacer," The Open Orthopaedics Journal, May 27, 2011, pp. 361-367, vol. 5.
Buric et al., "DIAM Device for Low Back Pain in Degenerative Disc Disease 24 Months Follow-up," Advances in Minimally Invasive Surgery and Therapy for Spine and Nerves, Alexandre et al., eds., 2011, pp. 177-182, Spinger-Verlat/Wien.
Phillips et al., "Biomechanics of Posterior Dynamic Stabiling Device (DIAM) After Facetectomy and Disectomy," The Spine Journal, 2006, vol. 6, pp. 714-722.
Taylor et al., "Device for Intervertebral Assisted Motion: Technique and Intial Results," 22 Neurosurg. Focus, Jan. 2007, vol. 22, No. 1, pp. 1-6.
Wilke et al., "Biomedical Effect of Different Lumbar Interspinous Implants on Flexibilty and Intradiscal Pressure," Eur Spine J., vol. 17, published online Jun. 27, 2008, pp. 1049-1056.
Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.
"Dispositivo Intervertebrale Ammortizzante DIAM," date unknown, p. 1.
"Tecnica Operatoria Per II Posizionamento Della Protesi DIAM," date unknown, pp. 1-3.
"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.
Benzel et al., "Posterior Cervical Interspinous Compression Wiring and Fusion for Mid to Low Cervical Spinal Injuries," J. Neurosurg., Jun. 1989, pp. 893-899, vol. 70.
Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.
Christie et al., "Dynamic Interspinous Process Technology," SPINE, 2005, pp. S73-S78, vol. 30, No. 16S.
Cousin Biotech, "Analysis of Clinical Experience with a Posterior Shock-Absorbing Implant," date unknown, pp. 2-9.
Cousin Biotech, Dispositif Intervertébral Amortissant, Jun. 1998, pp. 1-4.
Cousin Biotech, Technique Operatoire de la Prothese DIAM, date unknown, Annexe 1, pp. 1-8.
Dickman et al., "The Interspinous Method of Posterior Atlantoaxial Arthrodesis," J. Neurosurg., Feb. 1991, pp. 190-198, vol. 74.
Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.
Duff, "Methyl Methacrylate in Spinal Stabilization," Techniques in Spinal Fusion and Stabilization, Hitchon et al., eds., 1995, pp. 147-151, Ch. 14, Thieme, New York.
Ebara et al., "Inoperative Measurement of Lumbar Spinal Instability," SPINE, 1992, pp. S44-S50, vol. 17, No. 3S.
Fassio et al., "Treatment of Degenerative Lumbar Spinal Instability L4-L5 by Interspinous Ligamentoplasty," Rachis, Dec. 1991, pp. 465-474, vol. 3, No. 6.
Fassio, "Mise au Point Sur la Ligamentoplastie Inter-Epineuse Lombaire Dans les Instabilites," Maîtrise Orthopédique, Jul. 1993, pp. 18, No. 25.
Garner et al., "Development and Preclinical Testing of a New Tension-Band Device for the Spine: the Loop System," Eur. Spine J., Aug. 7, 2002, pp. S186-S191, vol. 11, Suppl. 2.
Guang et al., "Interspinous Process Segmental Instrumentation with Bone-Button-Wire for Correction of Scoliosis," Chinese Medical J., 1990, pp. 721-725, vol. 103.
Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.
Hambly et al., "Tension Band Wiring-Bone Grafting for Spondylolysis and Spondylolisthesis," SPINE, 1989, pp. 455-460, vol. 14, No. 4.
Kiwerski, "Rehabilitation of Patients with Thoracic Spine Injury Treated by Spring Alloplasty," Int. J. Rehab. Research, 1983, pp. 469-474, vol. 6, No. 4.
Kramer et al., "Intervetertebral Disk Diseases: Causes, Diagnosis, Treatment and Prophylaxis," pp. 244-249, Medical, 1990.
Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.
Mah et al., "Threaded K-Wire Spinous Process Fixation of the Axis for Modified Gallie Fusion in Children and Adolescents," J. Pediatric Othopaedics, 1989, pp. 675-679, vol. 9.
Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.
McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.
Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.
Müller, "Restauration Dynamique de la Stabilité Rachidienne," Tiré de la Sulzer Technical Review, Jan. 1999, Sulzer Management Ltd, Winterthur, Switzerland.
Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.
Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.
Petrini et al., "Stabilizzazione Elastica," Patologia Degenerativa del Rachide Lombare, Oct. 5-6, 2001, Rimini.
Porter, "Spinal Stenosis and Neurogenic Claudication," SPINE, Sep. 1, 1996, pp. 2046-2052, vol. 21, No. 17.
Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.
Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.
Richards et al., "The Treatment Mechanism of an Interspinous Process Implant for Lumbar Neurogenic Intermittent Claudication," SPINE, 2005, pp. 744-749, vol. 30, No. 7.
Scarfò, "Instability/Stenosis: Holistic Approach for Less Invasive Surgery," date unknown, University of Siena, Siena, Italy.
Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.
Schlegel et al., "The Role of Distraction in Improving the Space Available in the Lumbar Stenotic Canal and Foramen," SPINE, 1994, pp. 2041-2047, vol. 19, No. 18.
Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zdeblick et al., "Two-Point Fixation of the Lumbar Spine Differential Stability in Rotation," SPINE, 1991, pp. S298-S301, vol. 16, No. 6, Supplement.

Zucherman et al., "Clinical Efficacy of Spinal Instrumentation in Lumbar Degenerative Disc Disease," SPINE, Jul. 1992, pp. 834-837, vol. 17, No. 7.

* cited by examiner

INTERSPINOUS PROCESS SPACER DIAGNOSTIC BALLOON CATHETER AND METHODS OF USE

BACKGROUND

This invention relates generally to the treatment of spinal conditions, and more particularly, to the treatment of spinal stenosis using devices for implantation between adjacent spinous processes.

The clinical syndrome of neurogenic intermittent claudication due to lumbar spinal stenosis is a frequent source of pain in the lower back and extremities, leading to impaired walking, and causing other forms of disability in the elderly. Although the incidence and prevalence of symptomatic lumbar spinal stenosis have not been established, this condition is the most frequent indication of spinal surgery in patients older than 65 years of age.

Lumbar spinal stenosis is a condition of the spine characterized by a narrowing of the lumbar spinal canal. With spinal stenosis, the spinal canal narrows and pinches the spinal cord and nerves, causing pain in the back and legs. It is estimated that approximately 5 in 10,000 people develop lumbar spinal stenosis each year. For patients who seek the aid of a physician for back pain, approximately 12%-15% are diagnosed as having lumbar spinal stenosis.

Common treatments for lumbar spinal stenosis include physical therapy (including changes in posture), medication, and occasionally surgery. Changes in posture and physical therapy may be effective in flexing the spine to decompress and enlarge the space available to the spinal cord and nerves—thus relieving pressure on pinched nerves. Medications such as NSAIDS and other anti-inflammatory medications are often used to alleviate pain, although they are not typically effective at addressing spinal compression, which is the cause of the pain.

Surgical treatments are more aggressive than medication or physical therapy, and in appropriate cases surgery may be the best way to achieve lessening of the symptoms of lumbar spinal stenosis. The principal goal of surgery is to decompress the central spinal canal and the neural foramina, creating more space and eliminating pressure on the spinal nerve roots. The most common surgery for treatment of lumbar spinal stenosis is direct decompression via a laminectomy and partial facetectomy. In this procedure, the patient is given a general anesthesia as an incision is made in the patient to access the spine. The lamina of one or more vertebrae is removed to create more space for the nerves. The intervertebral disc may also be removed, and the adjacent vertebrae may be fused to strengthen the unstable segments. The success rate of decompressive laminectomy has been reported to be in excess of 65%. A significant reduction of the symptoms of lumbar spinal stenosis is also achieved in many of these cases.

More recently, a different surgical technique has been developed in which the vertebrae are distracted and an interspinous process spacer is implanted between adjacent spinous processes to maintain the desired separation between the segments. Currently, patient selection is based on history, physical examination, and imaging. These diagnostic modalities might be sensitive and specific to lumbar spinal stenosis, but they are limited in their ability to identify the proper interspinous process spacer candidate. Properly selecting the patients to receive an interspinous process spacer is important in assuring positive outcomes following implantation of the spacer.

It would thus be advantageous for a diagnostic device and procedure to be used to determine (i) whether an interspinous process spacer would provide relief for the patient, and (ii) the size of such a spacer that would be necessary to provide such relief. Such a diagnostic procedure could be performed in a doctor's office or other outpatient setting in addition to a standard hospital setting.

SUMMARY

The interspinous process spacer diagnostic balloon catheter (the "balloon catheter") described herein may be disposable. It may be inserted percutaneously into the interspinous space to temporarily decompress the identified spinal motion segment and allow a physician to determine whether the patient is an appropriate candidate for implantation of an interspinous process spacer. A method of diagnosing patients to determine if they are appropriate candidates for implantation of an interspinous process spacer is also disclosed herein.

The interspinous process spacer diagnostic balloon catheter has a main expandable member having a first collapsed configuration that allows percutaneous delivery of the distal portion of the balloon catheter to the appropriate site in the patient. The main expandable member can be expanded to different diameters, which is controlled by the physician, to provide the physician with control over the amount of decompression or distraction provided to the particular patient being diagnosed. In addition, two additional expandable members are located adjacent to the main expandable member, with one of the additional expandable members located on the proximal side of the main expandable member and the second additional expandable member located on the distal side of the main expandable member. The two additional expandable members, when expanded, hold the main expandable member in the proper location between adjacent spinous processes. The main expandable member may be formed from a relatively non-compliant material while the additional expandable members may be formed from a relatively compliant material.

A method of using the balloon catheter described herein is also provided. Once the main expandable member is properly located within the patient, the additional expandable members are expanded first to lock the main expandable member in place between adjacent spinous processes. Thereafter, the main expandable member is expanded to an initial size. At that point, the balloon catheter can be manipulated to allow the patient to become ambulatory to determine if the symptoms of lumbar spinal stenosis have been alleviated. If not, the main expandable member can be expanded to a second size, the device manipulated, and the patient becomes ambulatory to determine the effect of the device on the patient. This process would continue until the symptoms have been allieviated or until the main expandable member reaches some upper limit on its size. Thereafter, all of the expandable members can be deflated to their initial collapsed configuration and the balloon catheter removed from the patient. If the patient realizes relief from the symptoms of lumbar spinal stenosis during the diagnostic procedure, the physician can schedule a follow up surgical procedure to implant an appropriately sized interspinous process spacer as determined during the diagnostic procedure. If the patient does not obtain relief, the physician may determine that the patient may not be a candidate for implantation of an interspinous process spacer and evaluate other options for the patient.

DETAILED DESCRIPTION

Figure 1:
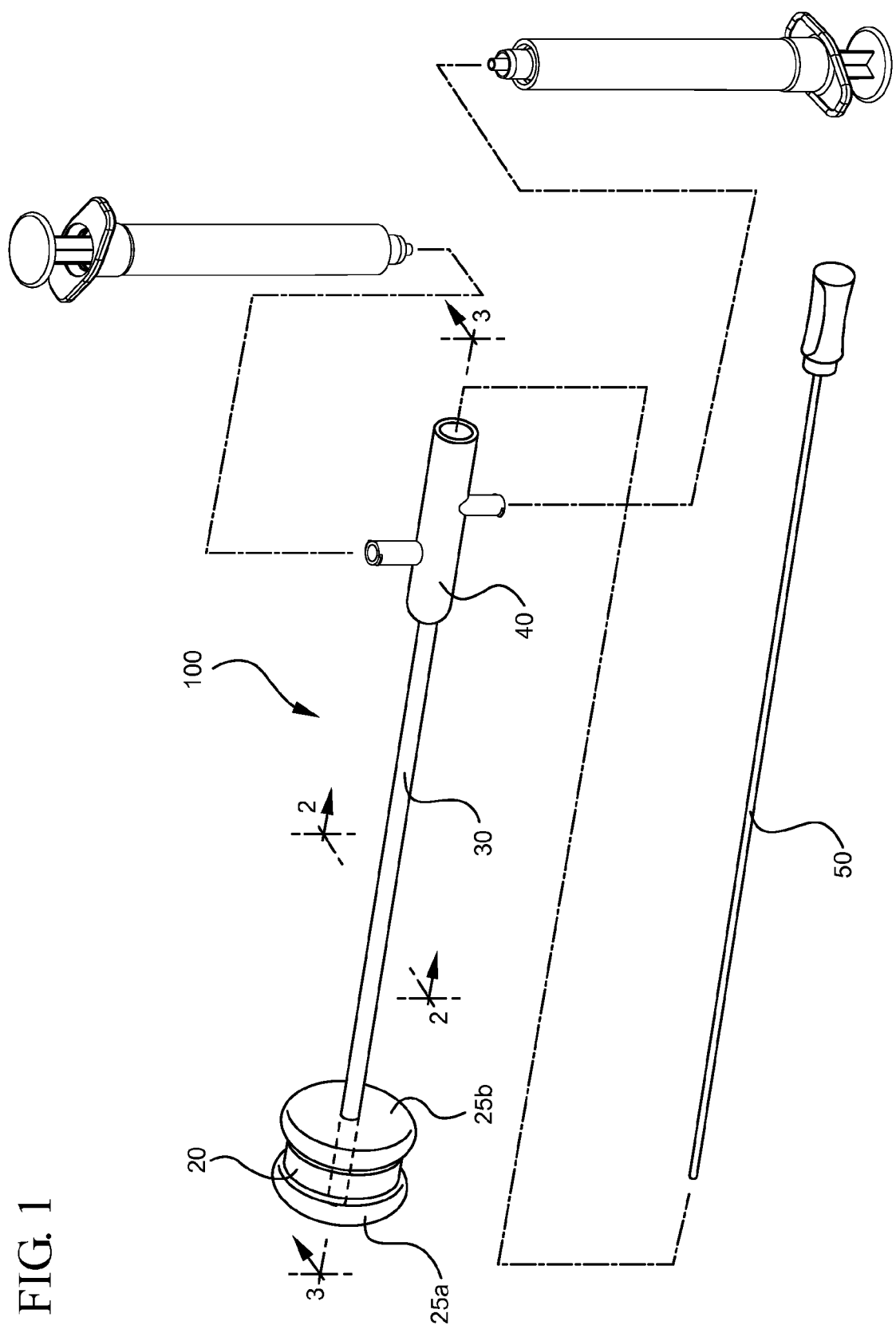
FIG. 1 is a perspective view of an interspinous process spacer diagnostic balloon catheter in the fully expanded configuration.

As used in this specification and the appended claims, the singular forms "a," "an" and "the" include plural referents unless the context clearly dictates otherwise. Thus, for example, the term "a member" is intended to mean a single member or a combination of members, and "a material" is intended to mean one or more materials, or a combination thereof. Furthermore, the words "proximal" and "distal" refer to directions closer to and away from, respectively, an operator (e.g., surgeon, physician, nurse, technician, etc.) who would insert the medical device into the patient, with the tip-end (i.e., distal end) of the device inserted inside a patient's body first. Thus, for example, the device end first inserted inside the patient's body would be the distal end of the device, while the device end last to enter the patient's body would be the proximal end of the device.

As used in this specification and the appended claims, the term "body" when used in connection with the location where the device is to be placed to treat lumbar spinal stenosis, or to teach or practice implantation methods for the device, means a mammalian body. For example, a body can be a patient's body, or a cadaver, or a portion of a patient's body or a portion of a cadaver.

As used in this specification and the appended claims, the term "parallel" describes a relationship, given normal manufacturing or measurement or similar tolerances, between two geometric constructions (e.g., two lines, two planes, a line and a plane, two curved surfaces, a line and a curved surface or the like) in which the two geometric constructions are substantially non-intersecting as they extend substantially to infinity. For example, as used herein, a line is said to be parallel to a curved surface when the line and the curved surface do not intersect as they extend to infinity. Similarly, when a planar surface (i.e., a two-dimensional surface) is said to be parallel to a line, every point along the line is spaced apart from the nearest portion of the surface by a substantially equal distance. Two geometric constructions are described herein as being "parallel" or "substantially parallel" to each other when they are nominally parallel to each other, such as for example, when they are parallel to each other within a tolerance. Such tolerances can include, for example, manufacturing tolerances, measurement tolerances or the like.

As used in this specification and the appended claims, the terms "normal", perpendicular" and "orthogonal" describe a relationship between two geometric constructions (e.g., two lines, two planes, a line and a plane, two curved surfaces, a line and a curved surface or the like) in which the two geometric constructions intersect at an angle of approximately 90 degrees within at least one plane. For example, as used herein, a line is said to be normal, perpendicular or orthoganal to a curved surface when the line and the curved surface intersect at an angle of approximately 90 degrees within a plane. Two geometric constructions are described herein as being "normal", "perpendicular", "orthogonal" or "substantially normal", "substantially perpendicular", "substantially orthogonal" to each other when they are nominally 90 degrees to each other, such as for example, when they are 90 degrees to each other within a tolerance. Such tolerances can include, for example, manufacturing tolerances, measurement tolerances or the like.

One embodiment of the interspinous process spacer diagnostic balloon catheter 100 is shown in the figures. Balloon catheter 100 is configured for unilateral insertion into the patient without requiring distraction of tissue on the contralateral side.

Balloon catheter 100 includes a main expandable member ("main balloon") 20, a distal expandable member ("distal balloon") 25a, and a proximal expandable member ("proximal balloon") 25b. All of these expandable members may be balloons formed from a relatively low compliant plastic such as nylon, polyethylene (PE) or polyethylene terephthalate (PET). Compliance is quantified based on the amount of change from the initially formed dimensions. Lower compliant materials are capable of stretching between about 5% to about 50% before failure, while a more compliant material such as polyurethane is capable of a change of about 300%. Generally, the lower the compliance of the balloon the higher its pressure capacity. Nylon and PET balloons are capable of withstanding a maximum pressure of about 300 psi. In contrast, a more compliant polyurethane balloon is capable of withstanding a maximum pressure of only about 125 psi.

Figure 3:
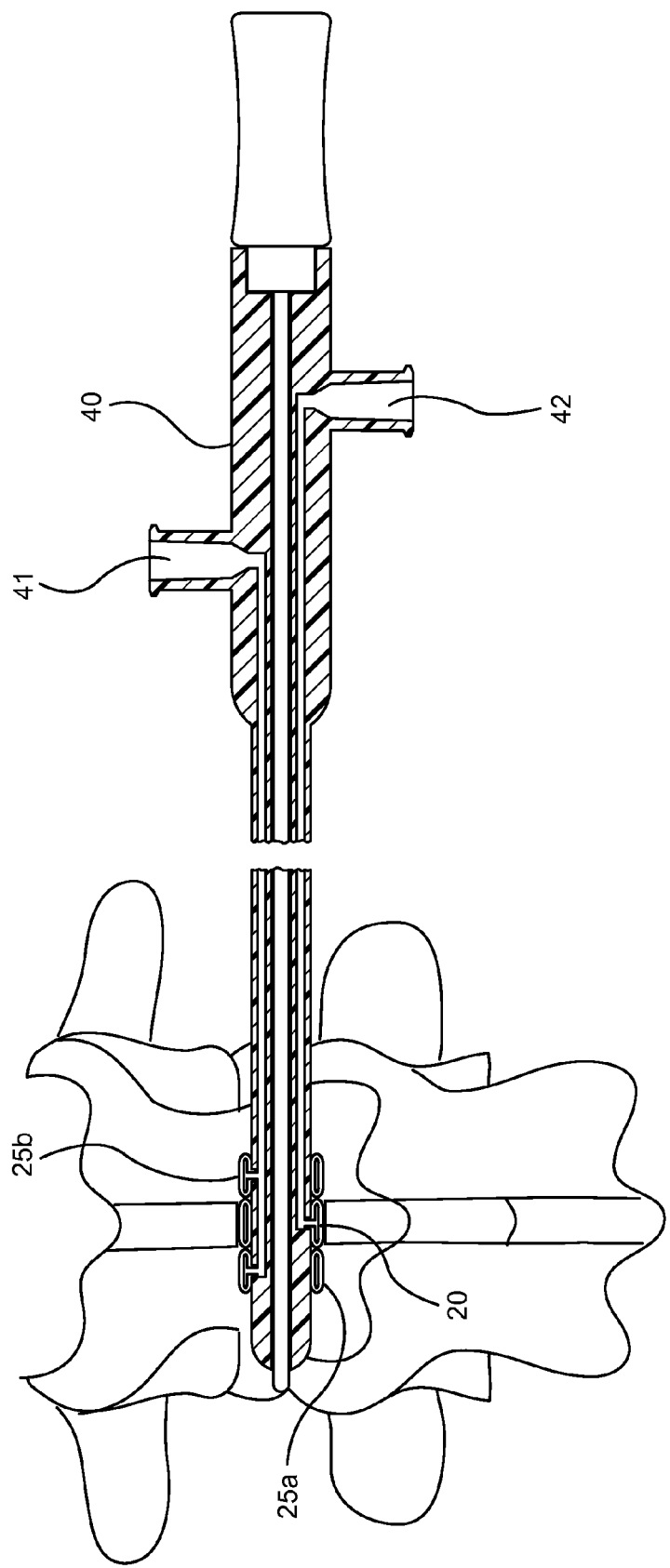
FIG. 3 is a cross-sectional view taken along line 3-3 of the interspinous process spacer diagnostic balloon catheter shown in FIG. 1 with the expandable members in the collapsed configuration and providing a schematic view of a portion of a spine where the interspinous process spacer diagnostic balloon catheter would be placed.
Figure 4:
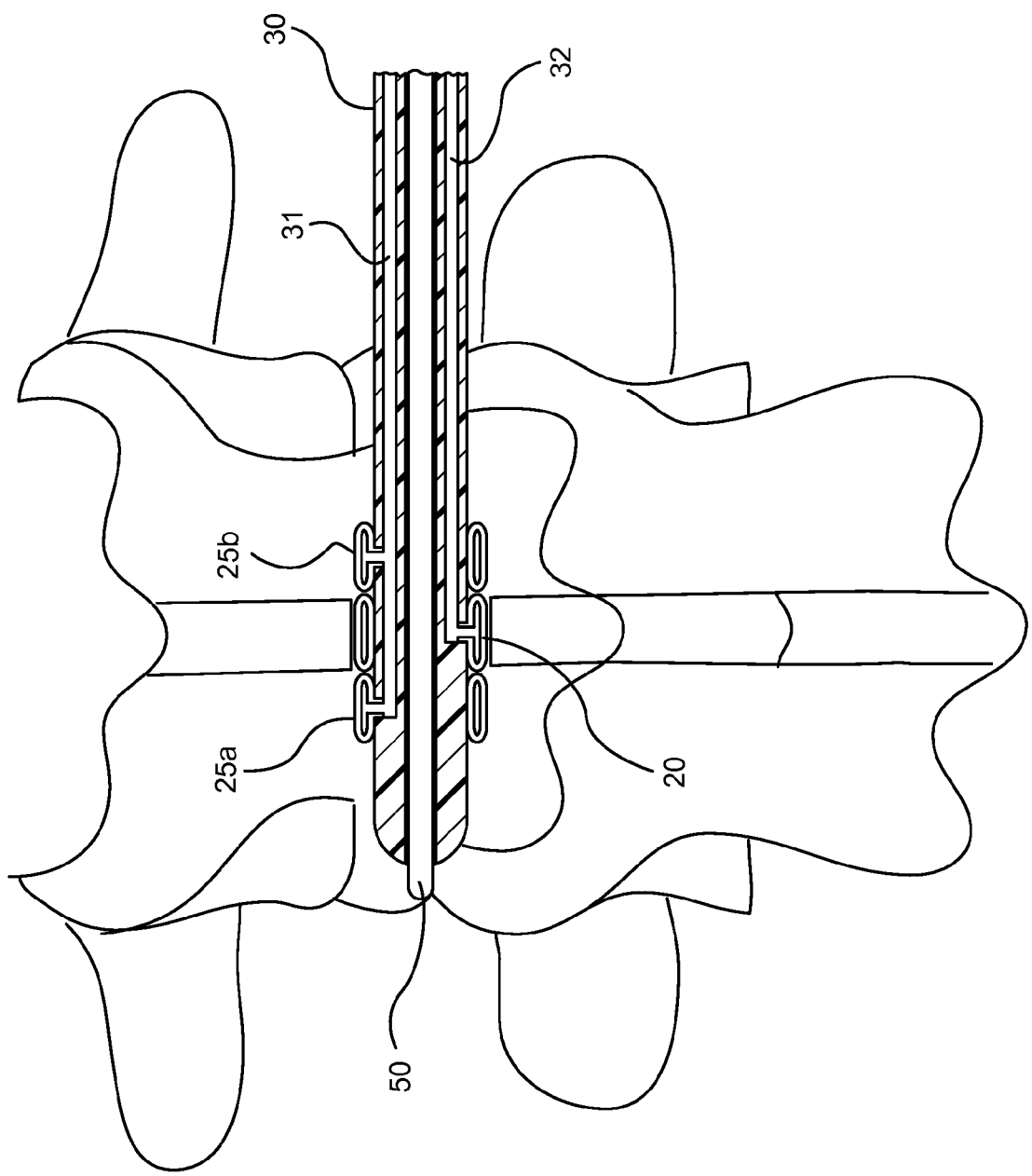
FIG. 4 is an enlarged cross-sectional view of the distal portion of the interspinous process spacer diagnostic balloon catheter shown in FIG. 3.
Figure 5:
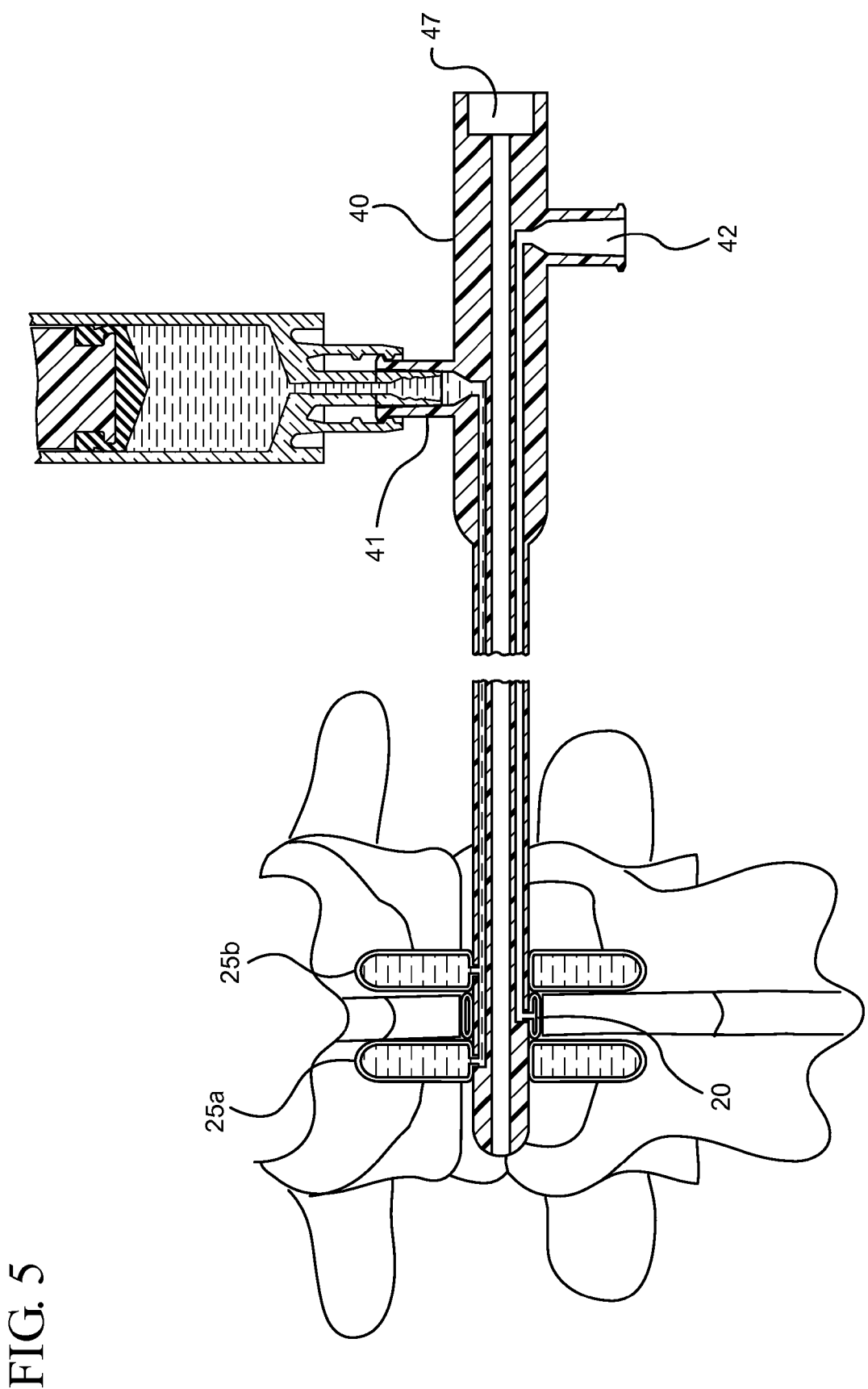
FIG. 5 is a cross-sectional view similar to FIG. 3 but with the proximal and distal expandable members in an expanded configuration.
Figure 6:
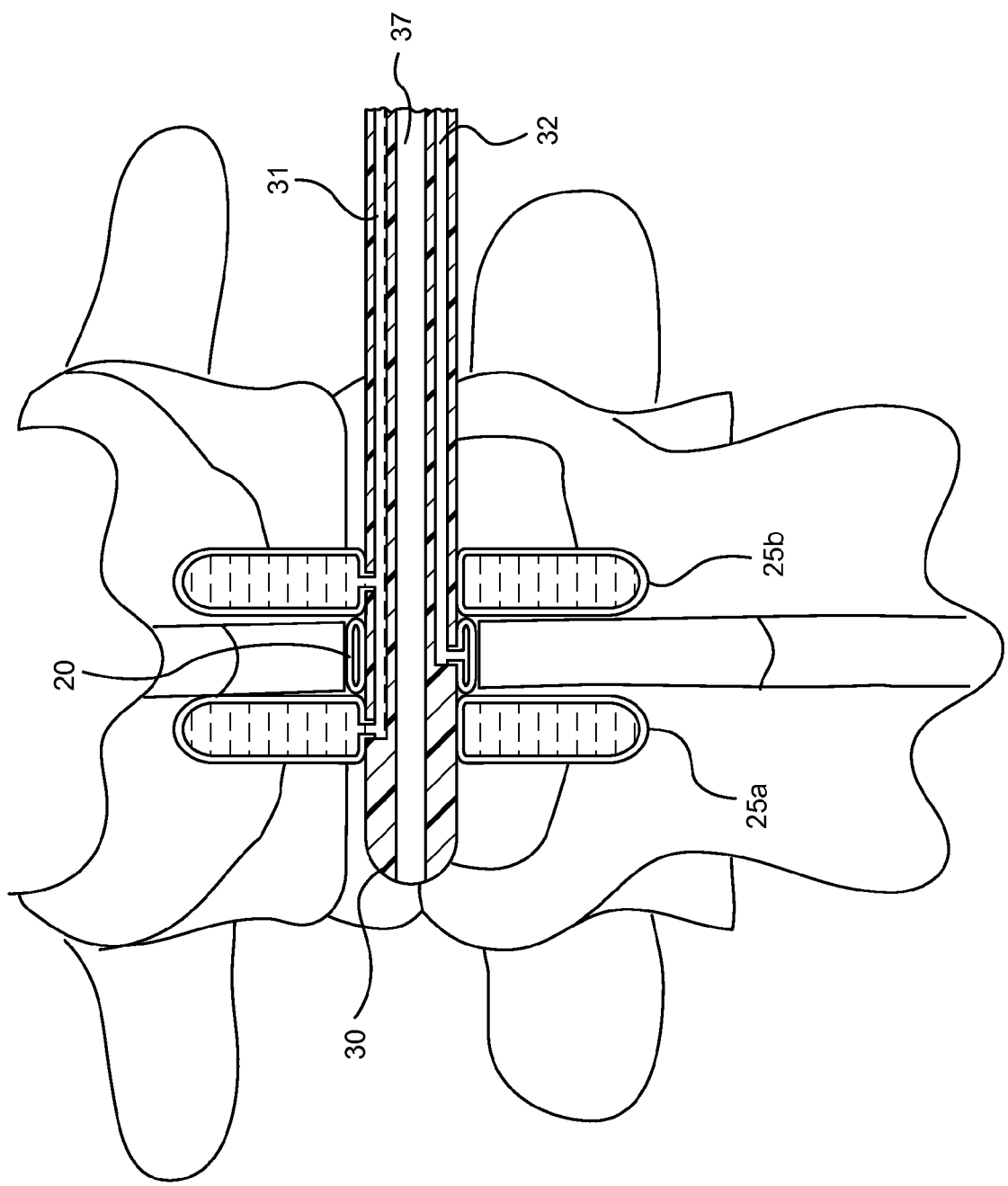
FIG. 6 is an enlarged cross-sectional view of the distal portion of the interspinous process spacer diagnostic balloon catheter shown in FIG. 5.
Figure 7:
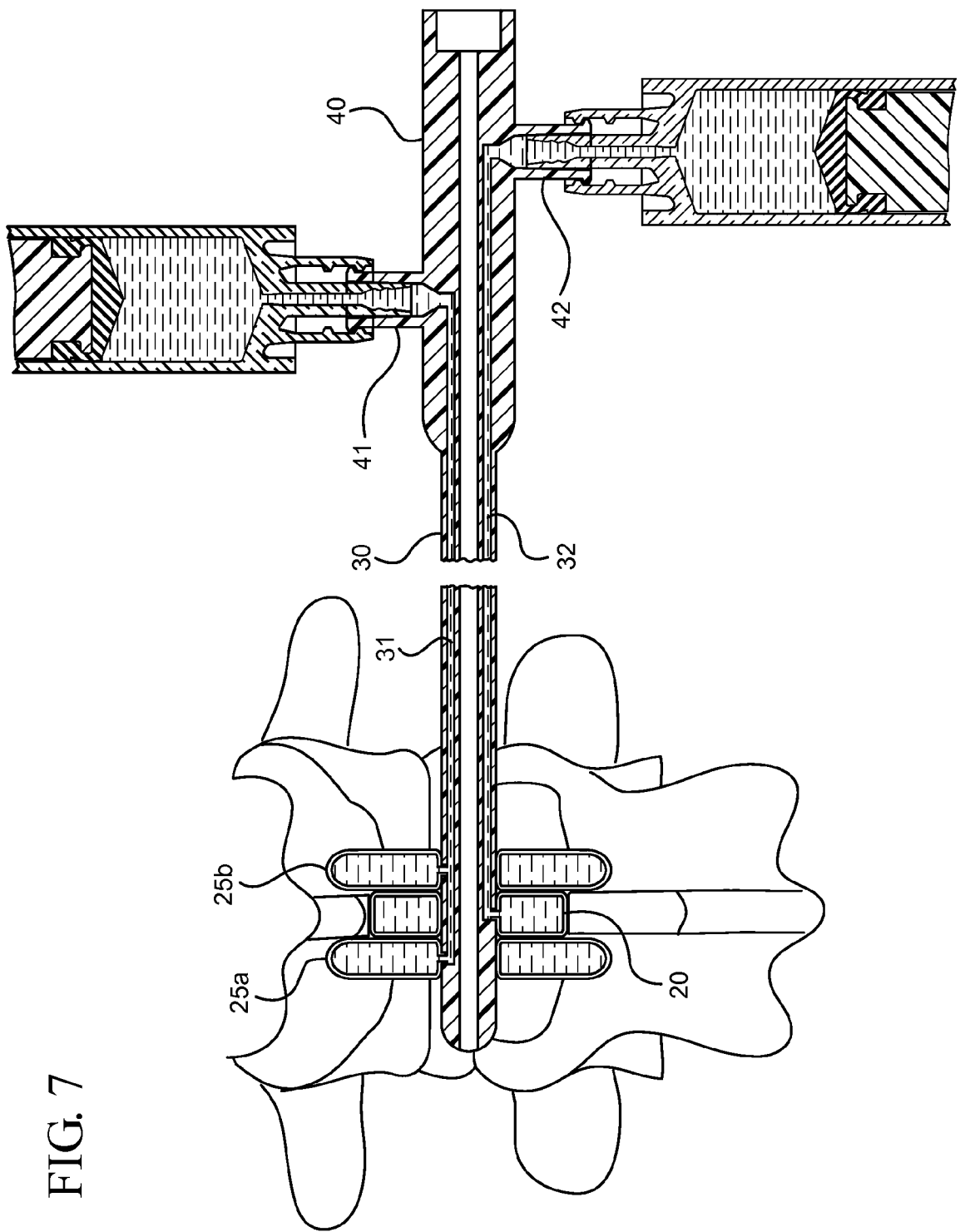
FIG. 7 is a cross-sectional view similar to FIG. 5 but with the main, central expandable member in the expanded configuration as well.
Figure 8:
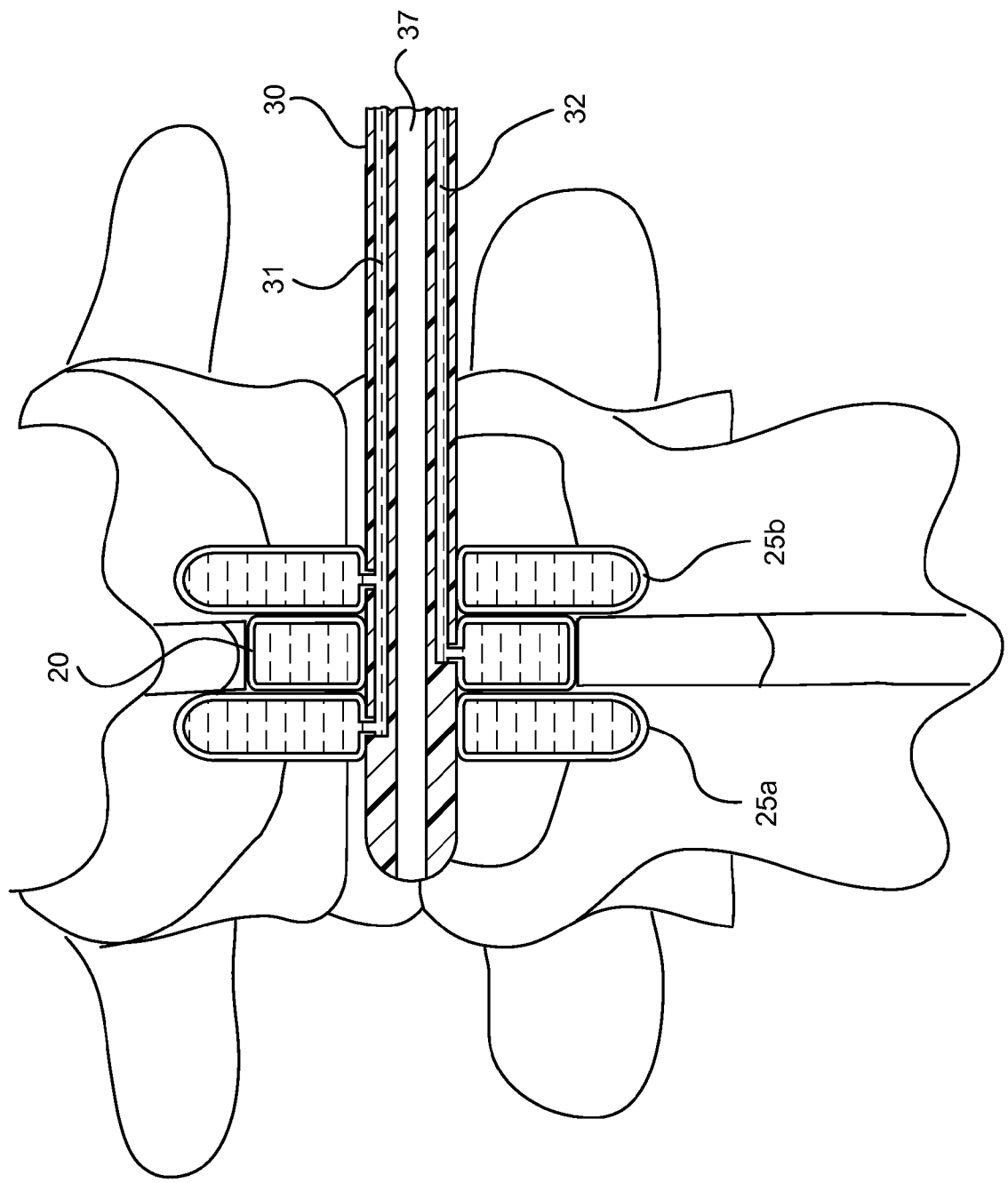
FIG. 8 is a cross-sectional view of the distal portion of the interspinous process spacer diagnostic balloon catheter shown in FIG. 7.

Main balloon 20 may be formed from a lower compliant material so that its inflation pattern is well controlled and understood. The inflation pattern, e.g. balloon diameter at specific volumes, will be used to determine the height of the interspinous space and thus the size of any permanent interspinous process spacer that is to be implanted into the patient to treat the condition. Also, the higher pressure capability of the lower compliant material may be instrumental in separating the spinous processes and maintaining the interspinous space. In contrast, distal balloon 25a and proximal balloon 25b may be formed from a more compliant material such as polyurethane, silicone or a thermoplastic rubber elastomer sold under the ChronoPrene™ trademark. Distal balloon 25a and proximal balloon 25b should be capable of expanding to a significantly larger diameter as compared to main balloon 20. A compliant material helps to minimize the profile of the distal portion of balloon catheter 100 and reduce the size of the incision necessary to access the particular location in the patient's anatomy. However, it is also within the scope of this invention to form distal balloon 25a and proximal balloon 25b from a less compliant material similar to the material used to form main balloon 20. This would facilitate catheter assembly, but the resulting device would require a larger access channel. Main balloon 20, distal balloon 25a and proximal balloon 25b are configured so they can move from a collapsed or closed configuration as illustrated in FIG. 3 to an expanded or deployed configuration as illustrated in FIGS. 1 and 8.

Main balloon 20, distal balloon 25a and proximal balloon 25b are affixed to a catheter 30 in a standard manner. For example, adhesives, thermal bonding, laser bonding or adhesive-lined heat shrinking may be used. In order to facilitate bonding of main balloon 20 to catheter tube 30, main balloon 20 may be formed from a three layer balloon tube where the middle layer is a less compliant material and the top and bottom layers are a more compliant material similar to the material used to form distal balloon 25a and proximal balloon 25b.

Distal balloon 25a and proximal balloon 25b may be inflated independently of main balloon 20. This would allow distal balloon 25a and proximal balloon 25b to be inflated first to lock balloon catheter 100 in place with main balloon 20 located between the desired adjacent spinous processes. Main balloon 20 could then be inflated separately and independently. Independent control of main balloon 20 may be necessary to correctly size the interspinous space. Alternatively, distal balloon 25a, main balloon 20 and proximal balloon 25b may be combined as a single balloon. Such a unitary configuration would mean that the single balloon would have a dumbbell shape with larger diameter distal and proximal portions and a smaller diameter central portion that all would be inflated simultaneously.

Figure 2B:
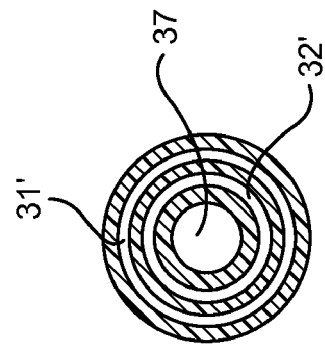
FIG. 2B is a cross-sectional view taken along line 2-2 of the interspinous process spacer diagnostic balloon catheter shown in FIG. 1 illustrating a second configuration for the catheter lumens.
Figure 2D:
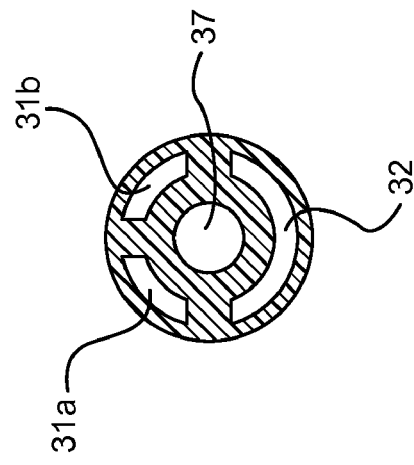
FIG. 2D is a cross-sectional view taken along line 2-2 of the interspinous process spacer diagnostic balloon catheter shown in FIG. 1 illustrating a fourth configuration for the catheter lumens.
Figure 2A:
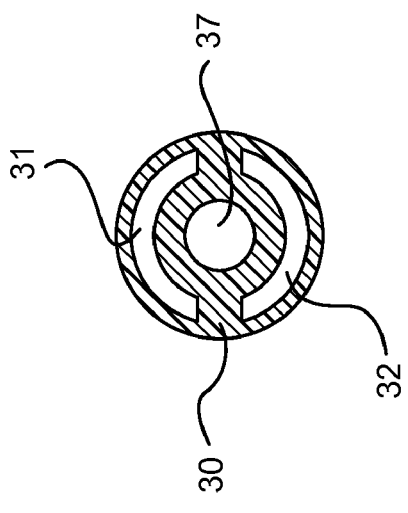
FIG. 2A is a cross-sectional view taken along line 2-2 of the interspinous process spacer diagnostic balloon catheter shown in FIG. 1 illustrating one configuration for the catheter lumens.
Figure 2C:
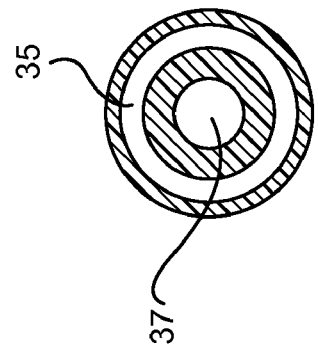
FIG. 2C is a cross-sectional view taken along line 2-2 of the interspinous process spacer diagnostic balloon catheter shown in FIG. 1 illustrating a third configuration for the catheter lumens.

Catheter tube 30 includes various lumens extending therethrough and that are used to expand the various balloons of balloon catheter 100. For example, as shown in FIG. 2A, a first lumen 31 is in fluid communication with both distal balloon 25a and proximal balloon 25b, while second lumen 32 is in fluid communication with main balloon 20. By having first lumen 31 in fluid communication with both distal balloon 25a and proximal balloon 25b, both balloons can be inflated simultaneously. Second lumen 32 is separate to allow main balloon 20 to be inflated separately once the physician locks the distal portion of balloon catheter 100 in place. In addition, a guide wire lumen 37 extends through catheter tube 30 to allow balloon catheter 100 to be inserted percutaneously over a guide wire. As shown in FIG. 2A, first lumen 31 extends around a portion of the axis of catheter tube 30, second lumen 32 extends around a separate portion of the axis of catheter tube 30 and guide wire lumen 37 is disposed coaxially between first lumen 31 and second lumen 32. If desired, distal balloon 25a and proximal balloon 25b could be in fluid communication with separate lumens. This will allow greater flexibility to the physician to initially position and adjust the specific location of the distal portion of balloon catheter 100 in the patient. For example, as shown in FIG. 2D, first lumen 31 could be split into two separate lumens 31a and 31b where lumen 31a could be in fluid communication with proximal balloon 25b and lumen 31b could be in fluid communication with distal balloon 25a or vice versa. These separate lumens would allow proximal balloon 25b to be inflated first, and deflated if necessary to reposition the distal portion of balloon catheter 100. Thereafter, distal balloon 25b could be inflated. Alternatively, distal balloon 25a could be inflated, and deflated if necessary, before proximal balloon 25b is inflated. Alternatively, the lumens may be oriented so they are all coaxial. See FIG. 2B. In this embodiment, first lumen 31' could be coaxially disposed within catheter tube 30, with second lumen 32' coaxially disposed between first lumen and guidewire lumen 37. In another embodiment, see FIG. 2C, a single lumen 35 may be in fluid communication with main balloon 20, distal balloon 25a and proximal balloon 25b. Single lumen 35 may be coaxially disposed about guidewire lumen 37. Alternatively a lumen configuration as should in FIG. 2A could be used without the need for second lumen 32.

The proximal end of catheter tube 30 is connected to a hub 40 having at least one port therein. The number of ports used depends on the lumen configuration desired for balloon catheter 100. Where a single lumen is used to inflate all three balloons, a single port is needed, in addition to any access device desired for the guidewire, if used. If two lumens are used, two ports are used. And where three lumens are used to inflate the three balloons, three ports are used. As an illustration, where the lumen configuration of FIG. 2A is used, a first port 41, a second port 42 and a guidewire port 47 are located on hub 40. First port 41 and second port 42 may each include a luer lock on its proximal end to allow an inflation device, such as a syringe to be locked on to each port. Guidewire port 47 allows a guide wire to extend completely through catheter tube 30 to facilitate proper placement of balloon catheter 100 between adjacent spinous processes as described more fully hereinafter. First port 41 and second port 42 each include seals, not shown, that allow independent control of the relevant balloons.

In the collapsed configuration, main balloon 20, distal balloon 25a and proximal balloon 25b each has a reduced profile that facilitates insertion of the distal end of balloon catheter 100 into the patient into the targeted interspinous space. If desired, a guidewire 50, may be first inserted into the patient so that it extends between the adjacent spinous processes under investigation. Balloon catheter 100 may then be inserted into the patient over the guidewire, with the guidewire extending through guidewire lumen 37, such that distal balloon 25a extends past the adjacent spinous processes of interest and is distal of the distal lateral faces of the superior spinous process and inferior spinous process. In this position, main balloon 20 is located between the adjacent spinous processes and proximal balloon 25b is located proximal of the other lateral faces of the superior spinous process and the inferior spinous process. At this point, distal balloon 25a and proximal balloon 25b may be expanded or "inflated" by injecting biocompatible fluid, such as saline, through first lumen 31 where the lumen configuration of FIG. 2A is used. Alternatively, where distal balloon 25a and proximal balloon 25b are to be inflated separately, such as by using the lumen configuration as shown in FIG. 2D, either distal balloon 25a or proximal balloon 25b may be inflated first to temporarily hold the distal portion of balloon catheter 100 in place while the physician confirms that the distal portion is properly located. If not, the initially inflated balloon may be deflated to allow the physician to properly relocate the distal portion of balloon catheter 100. This process may be repeated until the physician is satisfied with the placement of balloon catheter 100. Once fully inflated, distal balloon 25a and proximal balloon 25b will have a height that is greater than the space between the adjacent spinous processes, and greater than the height of main balloon 20 when it is fully inflated. Since distal balloon 25a and proximal balloon 25b are relatively compliant, they can conform better to the surrounding anatomy to hold balloon catheter 100 in place. Thus, with distal balloon 25a and proximal balloon 25b fully inflated, balloon catheter 100 is held in place in the patient's anatomy such that main balloon 20 is located between the adjacent spinous processes.

With main balloon 20 properly positioned, the physician can then inflate main balloon 20 by injecting a biocompatible fluid, such as saline, through second lumen 32 when the lumen configuration of FIG. 2A is used. Main balloon 20 has a predetermined geometry at fixed volumes. Thus, during inflation of main balloon 20, the physician will note the volume of fluid that is injected into main balloon 20. At a first volume corresponding to a particular diameter for main balloon 20, the physician will allow the patient to become ambulatory and seek feedback from the patient to determine if the amount of distraction represented by the first volume of fluid injected into main balloon 20 provides pain relief for the patient. If there is no pain relief, the physician can inject an additional volume of fluid into main balloon 20 representing a larger diameter for main balloon 20. The physician again allows the patient to become ambulatory and seeks feedback from the patient regarding any pain relief. This process continues until the patient experiences pain relief of the maximum rated volume of fluid has been injected into main balloon 20. If the patient experiences pain relief, the injected volume of fluid can be matched to the geometry of a permanent interspinous process spacer that would be permanently implanted in the patient. If the patient does not experience pain relief the physician may determine that the patient is not a candidate for the implantation of an interspinous process device.

The geometry of main balloon 20 includes a diameter that represents the distance between the adjacent spinous processes. The geometry also includes a width for main balloon 20 that should be approximately the width of a typical spinous process, or slightly larger. This ensures that main balloon 20 is provided with enough surface area to engage the adjacent spinous processes and also prevents force from concentrating along a smaller portion of the adjacent spinous processes. In such a situation, it is possible for osteoporotic bone, or bone that has been weakened, such as by disease or trauma, to fracture. The performance characteristics of main balloon 20, distal balloon 25a and proximal balloon 25b should be balanced against the desire to have a small profile for balloon catheter 100 when main balloon 20, distal balloon 25a and proximal balloon 25b are folded to facilitate the insertion of balloon catheter 100 to the proper location in the patient's anatomy.

Figure 9:
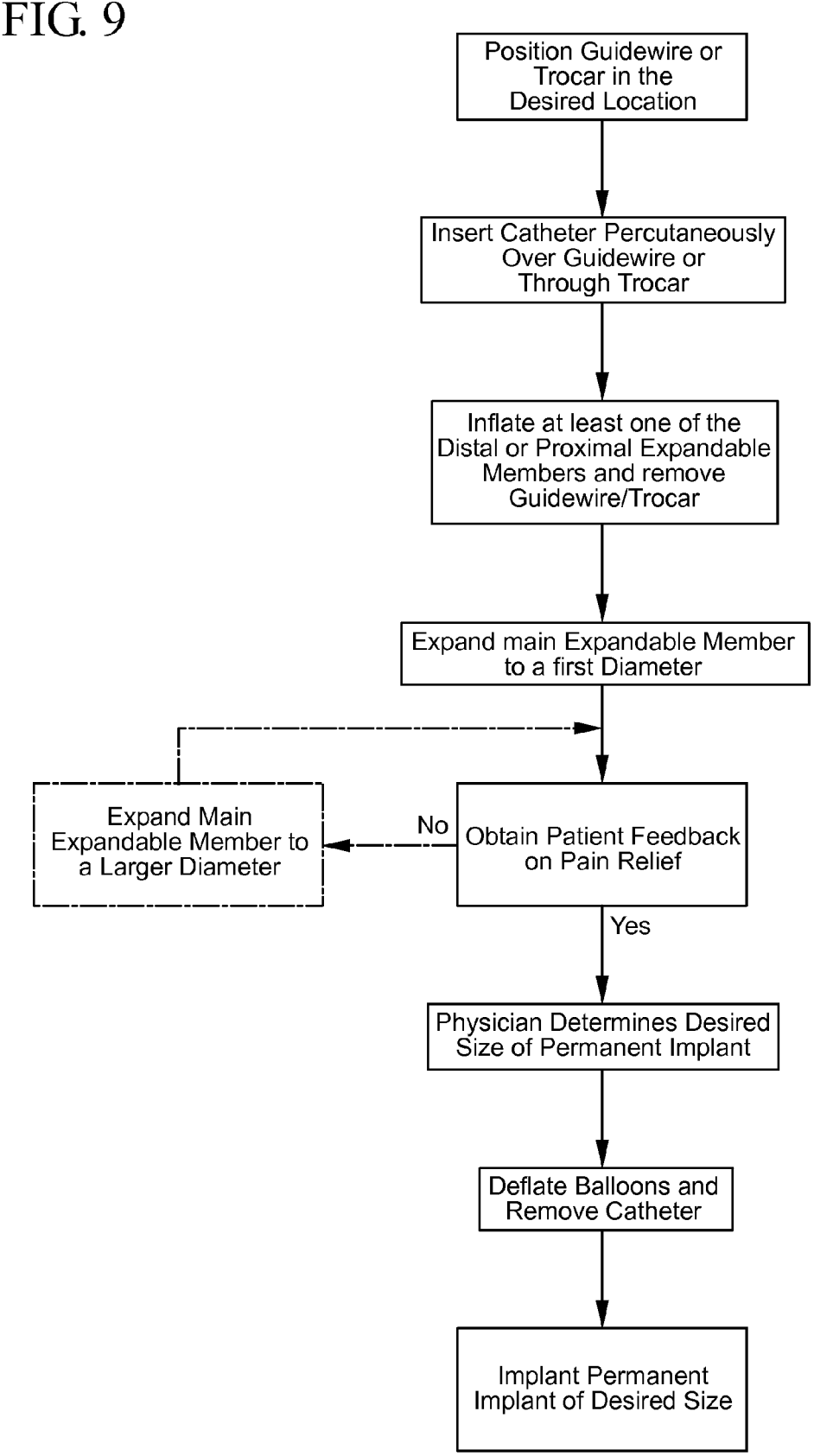
FIG. 9 is a flowchart describing a diagnostic method using an interspinous process spacer diagnostic balloon catheter.

FIG. 9 is a flow chart illustrating a method of using an interspinous process spacer diagnostic balloon catheter to determine whether a particular patient is a candidate for implantation of an interspinous process spacer to alleviate the symptoms of lumbar spinal stenosis. The interspinous process space under investigation is first accessed with a guidewire or a trocar such that the distal end of the guidewire or trocar is adjacent to the desired location. Balloon catheter 100 is then inserted percutaneously over the guidewire or through the trocar to position main balloon 20 in the interspinous space. If desired, the guidewire or trocar can be removed from the patient. Distal balloon 25a and proximal balloon 25b are ultimately expanded to hold the distal portion of balloon catheter 100 in place. Main balloon 20 is then expanded to a first expanded diameter. The patient then walks to determine if main balloon 20 has any affect on the lumbar spinal stenosis symptoms. If the pain has been alleviated, the physician notes the volume of fluid used to expand main balloon 20 and thus can determine the diameter of main balloon with that volume of fluid injected into main balloon 20. Fluid is then withdrawn from main balloon 20 so it collapses and balloon catheter 100 can then be removed from the patient. The physician uses the information from this diagnostic procedure to determine the size of an interspinous process spacer that can be used to treat the patient and schedules a follow up procedure to implant such a device. If the pain is not alleviated, the physician may expand main balloon 20 to a second expanded diameter. The patient then walks again to determine if there has been any pain relief. This process continues until the patient obtains relief or until main balloon 20 has reached its maximum rated diameter. If main balloon 20 reaches its maximum rated diameter, or if the physician so judges, the physician can conclude that the patient is not a candidate for an interspinous process spacer to treat lumbar spinal stenosis. The physician can then evaluate other treatment options for the patient.

Instead of using a single device having an expandable member that is expanded to different diameters, different devices having different sized expandable members may be inserted into the patient and then removed and replaced with a larger expandable member if the previous expandable member did not provide relief. This process is less desirable because of the additional material and process steps that need to be used and performed in order to achieve the information obtained using the method described above.

Balloon catheter 100 may be used in connection with a living patient for the treatment of various spinal disorders. Balloon catheter 100 may also be used in a non-living object, such as within a cadaver, model, and the like. The non-living object may be for one or more of testing, training, and demonstration purposes.

The elements of balloon catheter 100 may be positioned in the patient to contact various vertebral members. This contact may include direct contact with balloon catheter 100 actually touching the vertebral members, and may also include indirect contact with balloon catheter 100 actually touching the surrounding ligaments and tissue. In both instances, balloon catheter 100 includes a similar effectiveness for treating the spinal disorder for which it was implanted.

The interspinous process spacer diagnostic balloon catheter may be carried out in other specific ways than those herein set forth without departing from the scope and essential characteristics described herein. The present embodiments are, therefore, to be considered in all respects as illustrative and not restrictive, and all changes coming within the meaning and equivalency range of the appended claims are intended to be embraced therein.

What is claimed is:

1. An interspinous process spacer diagnostic balloon catheter, comprising:
   an elongate member;
   a main expandable member connected to a distal portion of the elongate member and configured for disposal between adjacent spinous processes, the main expandable member comprises a height equal to a distance between adjacent spinous processes and a width substantially equal to the width of a typical spinous process;
   a distal expandable member connected to a distal portion of the elongate member adjacent to a distal end of the main expandable member and configured for disposal on a distal side of adjacent spinous processes;
   a proximal expandable member connected to a distal portion of the elongate member adjacent to a proximal end of the main expandable member and configured for disposal adjacent spinous processes on an opposite side of the distal expandable member; and a plurality of lumens disposed in the elongate member in communication with one or more of the main expandable member, the distal expandable member and the proximal expandable member, wherein the proximal and distal expandable members each have a height that is greater than the distance between adjacent spinous processes and greater than the height of the main expandable member, wherein the distal expandable member and the proximal expandable member are configured to lock the diagnostic balloon catheter in place.

2. The catheter of claim 1 wherein the main expandable member is formed from a relatively non-compliant material.

3. The catheter of claim 1 wherein the distal expandable member and the proximal expandable member are formed from a relatively compliant material.

4. The catheter of claim 2 wherein the distal expandable member and the proximal expandable member are formed from a relatively compliant material.

5. The catheter of claim 4 wherein the main expandable material is formed from a three layer material having a middle layer, an inner layer and an outer layer.

6. The catheter of claim 5 wherein the middle layer is a relatively non-compliant material.

7. The catheter of claim 6 wherein the inner layer and the outer layer are a relatively compliant material.

8. The catheter of claim 1 wherein the lumens are coaxial.

9. The catheter of claim 1 wherein the elongate member defines at least two lumens extending therein wherein one lumen is in fluid communication with the distal expandable member and the proximal expandable member and one lumen is in fluid communication with the main expandable member.

10. The catheter of claim 9 wherein the two lumens extend coaxially in the elongate member.

11. The catheter of claim 1 wherein the elongate member defines one lumen extending therein wherein the one lumen is in fluid communication with the distal expandable member, the main expandable member and the proximal expandable member.

12. The catheter of claim 11 wherein the lumen extends coaxially in the elongate member.

13. The catheter of claim 1 wherein the elongate member defines at least three lumens extending therein wherein one lumen is in fluid communication with the distal expandable member, one lumen is in fluid communication with the main expandable member and one lumen is in fluid communication with the proximal expandable member.

14. A method of diagnosing a spinal disorder of a patient, comprising:

unilaterally inserting an expandable member while in a closed orientation into an interspinous space between adjacent spinous processes of the patient, with the expandable member in a closed configuration;

inflating expanding the expandable member to a first expanded diameter size;

thereafter, identifying whether the patient experiences pain relief when the expandable member is expanded to the first expanded size and disposed in the interspinous space diameter;

thereafter, deflating the expandable member to collapse collapsing the expandable member to a size smaller than the first expanded size;

thereafter, removing the expandable member from the interspinous space;

thereafter, implanting an interspinous process spacer into the Interspinous space, the spacer selected based on whether the patient experiences pain relief when the expandable member is expanded to the first expanded size patient.

15. The method of claim 14 further comprising expanding the expandable member to a second expanded size after identifying whether the patient experiences pain relief when the expandable member is expanded to the first size, and prior to the removing the expandable member.

16. The method of claim 14 wherein the expandable member is a central portion of a diagnostic spacer, and wherein the diagnostic spacer further comprises a distal balloon section and a proximal balloon section disposed on opposing lateral sides of the central portion, the method further comprising: after the inserting and prior to the identifying, expanding at least one of the proximal and distal balloon sections by inflation thereof.

17. The method of claim 16 wherein the expanding the at least one of the proximal and distal balloon sections occurs prior to the inflating of the expandable member.

18. The method of claim 14 wherein the expandable member is a central portion of a diagnostic spacer, and wherein the diagnostic spacer further comprises a distal balloon section and a proximal balloon section disposed on opposing lateral sides of the central portion, the method further comprising: after the inserting and prior to the identifying, expanding both the proximal and distal balloon sections by inflation thereof independently of the inflating of the expandable section.

19. The method of claim 14 wherein identifying whether the patient experiences pain relief comprises receiving feedback from the patient after the patient has become ambulatory with the first expandable member expanded to the first size.

20. The method of claim 14 further comprising selecting the interspinous process spacer based on both the first expanded size and whether the patient experiences pain relief with the expandable member expanded to the first size.

* * * * *